(12) United States Patent
Labreche et al.

(10) Patent No.: US 10,942,156 B2
(45) Date of Patent: Mar. 9, 2021

(54) METHOD FOR IDENTIFYING AN ANALYTE IN A FLUID

(71) Applicant: ALPHA M.O.S, Toulouse (FR)

(72) Inventors: Saïd Labreche, Buzet-sur-Tarn (FR); Olivier Cabrol, Toulouse (FR); François Loubet, Avignonet-Lauragais (FR); Hervé Lechat, Ramonville Saint Agne (FR); Sandrine Isz, Toulouse (FR); Jean-Christophe Mifsud, Goudourville (FR)

(73) Assignee: ALPHA M.O.S., Toulouse (FR)

( * ) Notice: Subject to any disclaimer, the term of this patent is extended or adjusted under 35 U.S.C. 154(b) by 677 days.

(21) Appl. No.: 15/569,456

(22) PCT Filed: Apr. 29, 2016

(86) PCT No.: PCT/EP2016/059618
§ 371 (c)(1),
(2) Date: Oct. 26, 2017

(87) PCT Pub. No.: WO2016/177639
PCT Pub. Date: Nov. 10, 2016

(65) Prior Publication Data
US 2018/0299416 A1    Oct. 18, 2018

(30) Foreign Application Priority Data

May 4, 2015  (EP) .................................. 15305680

(51) Int. Cl.
*G01N 30/86*  (2006.01)
*G01N 30/78*  (2006.01)
(Continued)

(52) U.S. Cl.
CPC ......... *G01N 30/8675* (2013.01); *G01N 30/78* (2013.01); *G01N 30/8631* (2013.01);
(Continued)

(58) Field of Classification Search
None
See application file for complete search history.

(56) References Cited

U.S. PATENT DOCUMENTS 5,801,297 A * 9/1998 Mifsud .................. G01N 33/14
                                                    73/23.34
5,827,946 A   10/1998 Klee et al.
(Continued)

FOREIGN PATENT DOCUMENTS

CN    201508353 U    6/2010
CN    103718031 A    4/2014
(Continued)

OTHER PUBLICATIONS

International Search Report for PCT/EP2016/059618, dated Aug. 7, 2016.
(Continued)

*Primary Examiner* — Gregory J Toatley, Jr.
*Assistant Examiner* — Terence E Stifter, Jr.
(74) *Attorney, Agent, or Firm* — Meagher Emanuel Laks Goldberg & Liao, LLP.

(57) ABSTRACT

The invention relates to a method for the identification of an analyte in a sample fluid. The method comprises the performance of a set of measurements on at least two sensors of different types. Sensors of different types may comprise Gas Chromatography sensors, CMOS gas sensors, a combination thereof, or more generally sensors in which it is possible to control a first physical parameter and measure, for different values of the first parameter, a second physical parameter representative of at least a concentration of the analyte. The method comprises the detection of maxima of the second parameter, the access to databases in order to find reference values of the first parameters in which maxima are
(Continued)

found, and the comparison of values at which maxima are found and reference values, on the two sensors.

13 Claims, 6 Drawing Sheets

(51) Int. Cl.
  *G01N 33/00* (2006.01)
  *G01N 27/12* (2006.01)
  *G01N 30/02* (2006.01)

(52) U.S. Cl.
  CPC ....... *G01N 33/0022* (2013.01); *G01N 27/124* (2013.01); *G01N 33/0031* (2013.01); *G01N 33/0032* (2013.01); *G01N 33/0034* (2013.01); *G01N 2030/025* (2013.01)

(56) References Cited

U.S. PATENT DOCUMENTS

| | | | |
|---|---|---|---|
| 2005/0252275 | A1 | 11/2005 | Kita et al. |
| 2012/0143515 | A1* | 6/2012 | Norman ............. G01N 33/0031 702/24 |
| 2014/0105790 | A1 | 4/2014 | Gaudon et al. |
| 2014/0274751 | A1 | 9/2014 | Sadowski et al. |
| 2016/0187279 | A1* | 6/2016 | Tayebi ................. G01N 27/123 73/23.21 |

FOREIGN PATENT DOCUMENTS

| | | |
|---|---|---|
| EP | 1582868 A1 | 10/2005 |
| JP | S5621063 A | 2/1981 |
| JP | H01260355 A | 10/1989 |
| JP | H11500821 A | 1/1999 |
| JP | 2005291715 A | 10/2005 |
| JP | 2014524568 A | 9/2014 |
| WO | 0060332 A2 | 10/2000 |

OTHER PUBLICATIONS

Written Opinion for PCT/EP2016/059618, dated Aug. 7, 2016.
English translation of JP Office Action for corresponding JP Patent Application No. 2017-557394 dated Sep. 25, 2018.
Robert L.Grob et all "Modern Practice of gaz chromatography" . Wiley Interscience . fourth Edition (2004).
A.Wehrli and E.Kovats. Gas-chromatographische Charakterisierung organischer Verbindungen. Teil 3: Berechnung der Retentionsindices aliphatischer, alicyclischer und aromatischer Verbindungen.Helv. Chim.Acta 42, 2709 (1959).
H. Nau et al.: "Computer-assisted assignment of retention indexes in gas chromatography-mass spectrometry and its application to mixtures of biological origin", Analytical Chemistry, vol. 46, No. 3, pp. 426-434; XP055225221; Mar. 1, 1974.
Xu, Xiao-Qing et al.: "Differences in volatile profiles of Cabernet Sauvignon grapes grown in two distinct regions of China and their responses to weather conditions", Plant Physiology and Biochemistry, vol. 89, pp. 123-133; XP029214527; Feb. 26, 2015.
English translation of Japanese Office Action issued in JP 2017-557394, dated Mar. 24, 2020.
English Translation of Chinese Office Action issued in corresponding CN 201680034906.2, dated Oct. 8, 2019.
Li Wenhai "Double-capillary column double detector gas chromathography for detection of common poisons", Chinese Journal of Forensic Medicine, vol. 21, No. 6, pp. 351-352, Dec. 31, 2006 [only Chinese document available].
Tan Guiliang et al. "Application of Modern Molecular Biology and omics Technology in Food Saftey Testing", Guangzhou: Sun Yat-Sen University Press, pp. 286-287, Jun. 30, 2014 [only Chinese document available].
Wang Weixin "Study on the method of electronic nose identification of traditional Chinese medicine", Full text database of excellent master degree theses of China medicine health technology section, No. 11, p. E057-7, Nov. 15, 2009 [only Chinese document available].

\* cited by examiner

- Identification criteria
  - File
  - Identification parameters — 440b
    - Column name: MXT-5-FID1     Tolerance  30  — 410b
    - Column name: MXT-1701-FID2              30  — 411b
    - Number of compounds per peak   5
  - ☑ Search according to compound features
    - ☑ Name and Synonyms  [       ] Containing ▼
    - ☑ Formula            [       ] Containing ▼
    - ☑ CAS #              [   ].[   ] Containing ▼
    - ☐ Molar mass         0.00 +or- 20.00
  - ☑ Search according application field — 420b
    - Environement
    - Flavors & Fragrances
    - Food
    - Forensic medicine
    - Herbicide
    - [>>] [<<]
    - ● And   ○ Or
  - ☑ Search according to sensory descriptor — 450b
    - Acetone
    - Acidic
    - Acidulous
    - Acorn
    - Acrid
    - Alcoholic
    - [>>] [<<]
    - ● And   ○ Or
  - ☑ Product Search
    - Product name [                ] — 430b

[Search] [Reset] [Cancel]

400b

Sample: CA030_045 ;Column :MXT-5-FID1 ;Peak :49.52/1045

| Name | Formula | DB-5 | DB-1701 | Relevence index | Difference-DB-5 | Difference-DB-1701 |
|---|---|---|---|---|---|---|
| L-Limonene | C10H16 | 1034 | 1061 | 13.66 | 10.87 | 4.06 |
| Limonene | C10H16 | 1033 | 1061 | 12.66 | 11.87 | 4.06 |
| Beta-phellandrene | C10H16 | 1030 | 1059 | 7.66 | 14.87 | 6.06 |
| 1-Methyl-4-isopropenyl-1-cyc | C10H16 | 1030 | 1056 | 4.66 | 14.87 | 9.06 |
| (Z)-2-octenal | C10H14O | 1045 | 1157 | 0.16 | 0.13 | 6.29 |
| benzeneacetaldehyde | C8H8O | 1043 | 1188 |  | 1.87 | 2.06 |
| 4-hydroxy-5-methyl-3(2H) -fu | C5H6O3 | 1043 | 1263 |  | 1.87 | 0.11 |
| Benzene,1,2-dichloro- | C6H4C12 | 1040 | 1109 |  | 4.87 | 11.06 |
| 2-Acetylpyridine | C7H7NO | 1039 | 1162 |  | 5.87 | 11.29 |
| Glycerol | C3H8O3 | 1037 | 1082 |  | 7.87 | 4.89 |
| Phenol,2-methyl- | C7H8O | 1054 | 1283 |  | 9.13 | 9.32 |
| Benzyl alcohol | C7H8O | 1034 | 1220 |  | 10.87 | 3.64 |

Name and Synonyms

Limonene

Formula: C10H16

CAS #: 5989-27-5

Molar mass (g/mol): 136

Sensory descriptors

| Citrus |
| Fruity |
| Minty |
| Orange |
| Peely |

Application Domains

Food

Kovats retention index

| | Value | Minimum | Maximum | Median | Mean | S-D | Number |
|---|---|---|---|---|---|---|---|
| DB-5 | 1033 | 995 | 1073 | 1030 | 1029 | 7 | 716 |
| DB-1701 | 1061 | 1047 | 1061 | 1054 | 1054 | 6 | 3 |
| DB-1 | 1023 | 982 | 1064 | 1023 | 1024 | 8 | 532 |
| DB-Wax | 1200 | 1106 | 1298 | 1200 | 1198 | 15 | 560 |
| DB-Wax | 1200 | 1178 | 1229 | 1200 | 1200 | 14 | 27 |

FIG.4c

METHOD FOR IDENTIFYING AN ANALYTE IN A FLUID

FIELD OF THE INVENTION

The present invention relates to the detection of chemical components. More specifically, it relates to statistical methods to improve selectivity of measurements using measurements of at least two different measurement types.

BACKGROUND PRIOR ART

Detection of chemical components designates the identification of the type and/or quantity of a chemical component. In the general field of chemical detection, an analyte designates a substance or component of particular interest for a chemical measurement. A transducer is an element that converts the information from a sensor into a physical signal (for example electrical intensity) representative of the detection of substance or components by the sensor. The sensitivity represents the ability of a sensor to detect even a small quantity of a component. The selectivity designates the ability to precisely determine the component that has been detected by a sensor.

A large number of biochemical sensors exist. For example, gas chromatography consists in passing gas components in a column. For a definite composition of a static phase in the column, each type of component is characterized by a specific duration for crossing the column, which is called retention time. In usual gas chromatography systems, a detector is placed at the end of the column, which outputs at any time a value representative of the quantity of components that leaves the column. A component that is present with a large concentration in a fluid processed in a gas chromatograph therefore generates a peak of intensity around the retention time characterizing the component. The analysis of gas chromatography peaks, and comparison with reference values for a set of analytes is a widely used method of determination of the type and quantity of components present in a fluid.

However, the selectivity of a gas chromatography sensor may be limited if several components have comparable retention times, or if the time resolution of the sensor at the end of the column is not high enough to disambiguate the peaks generated by two different analytes.

CMOS gas sensors, for example metal oxide gas sensors form another family of biochemical sensors for the detection of components in a gas. A metal oxide gas sensor modifies the sensitivity of an electrical component according to the concentration of some components in a gas, and parameters specific to the sensor, such as the chemical composition of the sensing layer, and the temperature at the surface of the layer. Some metal oxide sensors are designed in terms of surface composition and temperature to precisely detect a single analyte. Such sensors usually possess a high selectivity to one analyte, but a very poor selectivity to other analytes. On the other hand, some metal oxide sensors are designed to generate measurement at various temperatures, the change of sensitivity due to each analyte varying with the temperature of the surface of the sensor. However, due to the large number of possible analytes and the possibility that many analytes modify the sensitivity of the sensor at the same temperature, the selectivity of such a sensor to a large number of analytes remains low. Such drawback may be mitigated by using 2D arrays of CMOS sensors, each sensor in an array being sensitive to different analytes in a gas. Also, 3D stacks of CMOS sensors can be used to increase selectivity of the sensor arrangement, such as those disclosed in the European patent application co-assigned to the applicant of this application which is published under n° EP2718705.

The determination of analytes in a fluid is generally based to a comparison of actual measurements with reference values obtained from a library. For example, in gas chromatography an analyte can be identified by comparing the retention time of a peak to a set of theoretical retention times for different analytes in the same gas chromatography column. However, the determination of the type of an analyte requires that a theoretical value already exists from a reliable source for this analyte. Due to the large number of possible analytes, it is therefore desirable to use theoretical data from a number of sources as large as possible.

In gas chromatography, the Kovats index is a generalization of the retention time of a compound for a type of column, a type of column being determined by the stationary phase of the column. The values of retention times for each peak can be converted, according to parameters such as the length of the columns, the temperature, etc to a Kovats index which only depends of a type of column, therefore allowing comparison between different columns having the same stationary phase, and the collaborative creation of large databases.

U.S. Pat. No. 6,153,438 discloses a method for determining that an unknown analyte is present in a fluid by comparing retention times in gas chromatography to known retention times in a database. However, the use of a single GC (gas chromatography) column type does not solve the issue of the selectivity of components when a plurality of analytes have close retention times. Also, according to the disclosure of this patent, it is not possible to identify the analyte. Similar methods exist for other types of sensors. For example, it is possible to build a database of the temperatures that correspond to peaks of sensitivity for given analytes for metal-oxide gas sensors, and use this database to determine a type of gas analyte according to the measurement from an unknown fluid.

The usual method for improving selectivity consists in improving the sensor themselves. However, the modification of a sensor implies that a new database has to be built for each analyte of interest. Due to the large number of possible analytes, this is a long and costly task. Moreover, the improvement of a single type of sensor may hardly improve the selectivity to all analytes. The same problem exists with the identification of other fluids, like liquids.

There is therefore a need of a method that improves the selectivity of biochemical sensors, without rebuilding a complete database for all analytes of interest.

SUMMARY OF THE INVENTION

To this effect, the invention discloses a method for identifying an analyte in a fluid sensed by a group of sensors comprising a first sensor and a second sensor of different types, said method comprising: obtaining a first set of values from the first sensor of at least a first and a second physical parameters, said first and parameter varying monotonically within a range of values, each value of the second parameter being associated with at least a value of the first parameter, said second parameter being representative of at least a concentration of the analyte and comprising at least a first local extremum for a first value of the first parameter; obtaining a second set of values from the second sensor of a third and a fourth parameter, said third parameter varying monotonically within a range of values, each value of the fourth parameter being associated with at least a value of the third parameter, said fourth parameter being representative of at least a concentration of the analyte and comprising at least a second local extremum for a second value of the third parameter; accessing at least a database of reference values of the first parameter from a sensor of the same type as the first sensor, and reference values of the third parameter from a sensor of the same type as the second sensor; searching said at least a database for a reference value of the first parameter in relation to an extremum of the second parameter, and a reference value of the third parameter in relation to an extremum of the fourth parameter.

Advantageously, the reference value of the first parameter is the value of the first parameter present in the at least a database which is the closest to the first value of the first parameter, and the reference value of the third parameter is the reference value of the third parameter present in the at least a database which is the closest to the second value of the third parameter.

Advantageously, the reference value of the first parameter is any value of the first parameter present in the at least a database, and the reference value of the third parameter is any value of the third parameter present in the at least a database.

Advantageously, the method further comprises calculating a first ratio between at least the first local extremum and at least the second local extremum.

Advantageously, the method further comprises obtaining a second ratio, said second ratio being calculated by a method comprising: obtaining a first additional set of values from the first sensor and a second additional set of values from the second sensor of at least the first and the second physical parameters, respectively the third and the fourth physical parameters, for a second fluid comprising a known analyte; searching the at least a database for an additional reference value of the first parameter in relation to an additional extremum of the second parameter in relation to the known analyte, and an additional reference value of the third parameter in relation to an additional extremum of the fourth parameter in relation to the known analyte; calculating the second ratio between at least the additional extremum of the second parameter in the first additional set of values and at least the additional extremum of the fourth parameter in the second additional set of values.

Advantageously, the at least a database further comprises reference values of the second parameter from a sensor of the same type than the first sensor, and reference values of the fourth parameter from a sensor of the same type than the second sensor, and the method further comprises: obtaining a second ratio, between at least a local extremum of the reference values of the second parameter in relation with the reference value of the first parameter and at least a local extremum of the reference values of the fourth parameter in relation with the reference value of the third parameter.

Advantageously, the method further comprises computing a score for the analyte, said score being obtained by performing at least the product of: a first additional ratio of the minimum of the second ratio and the first ratio to the maximum of the second ratio and the first ratio; a second additional ratio of the minimum of the first value of the first parameter and the reference value of the first parameter to the maximum of the first value of the first parameter and the reference value of the first parameter; a third additional ratio of the minimum of the second value of the third parameter and the reference value of the third parameter to the maximum of the second value of the third parameter and the reference value of the third parameter.

Advantageously, at least one of the first and the second sensor is a Gas Chromatography Column and at least one the first and the third physical parameter is one of a retention time and a Kovats index.

Advantageously, the second ratio is a ratio of two surfaces under a peak of intensity of a Gas Chromatography column.

Advantageously, at least a database is the NIST database.

Advantageously, at least one of the first and the second sensor is a metal oxide sensor, at least one of the first and the third physical parameter is one of a temperature, a wavelength of an UV illumination, and an intensity of an electric pulse, and at least one of the second and the first physical parameter is a value of sensitivity.

The invention also discloses a method for identifying an analyte in a sample of fluid sensed by a group of sensors comprising at least three sensors, comprising performing the steps of a method for identifying an analyte in a fluid sensed by a group of sensors comprising a first sensor and a second sensor of different types according to the invention.

Advantageously, the method comprises computing a global score the analyte as the average value of all scores for all possible pairs of sensors.

Advantageously, the method comprises displaying to an operator a plurality of scores for a plurality of analytes.

The invention also discloses a device for identifying an analyte in a fluid sensed by a group of sensors comprising a first sensor and a second sensor of different types, said device comprising: a first module configured for: obtaining a first set of values from the first sensor of at least a first and a second physical parameters, said first parameter varying monotonically within a range of values, each value of the second parameter being associated with at least a value of the first parameter, said second parameter being representative of at least a concentration of the analyte and comprising at least a first local extremum for a first value of the first parameter; obtaining a second set of values from the second sensor of at least a third and a fourth physical parameters, said third parameter varying monotonically within a range of values, each value of the fourth parameter being associated with at least a value of the third parameter, said fourth parameter being representative of at least a concentration of the analyte and comprising at least a second local extremum for a second value of the fourth parameter; a second module configured for accessing at least a database of reference values of the first parameter from a sensor of the same type than the first sensor, and reference values of the third parameter from a sensor of the same type as the second sensor; a third module configured for searching said at least a database for a reference value of the first parameter in relation to an extremum of the second parameter, and a reference value of the third parameter in relation to an extremum of the fourth parameter.

The invention also discloses a computer program product, stored on a computer readable medium, configured for identifying an analyte in a fluid sensed by a group of sensors comprising a first sensor and a second sensor of different types, said computer program product comprising: code means for obtaining a first set of measured values from the first sensor of at least a first and a second physical parameters, said first parameter varying monotonically within a range of values, each value of the second parameter being associated with at least a value of the first parameter, said second parameter being representative of at least a concentration of the analyte and comprising at least a first local extremum for a first measured value of the first parameter; code means for obtaining a second set of measured values from the second sensor of a third and a fourth physical parameters, said third parameter varying monotically within a range of values, each value of the fourth parameter being associated with at least value of the third parameter, said fourth parameter being representative of at least a concentration of the analyte and comprising at least a second local extremum for a second measured value of the third parameter; code means for accessing at least a database of reference values of the first parameter from a sensor of the same type than the first sensor, and reference values of the third parameter from a sensor of the same type as the second sensor; code means for searching said at least a database for a reference value of the first parameter in relation to an extremum of the second parameter, and a reference value of the third parameter in relation to an extremum of the fourth parameter.

A method according to the invention is able to identify analytes with an optimal comparison of values from various sensors.

A method according to the invention is able to disambiguate a type of analyte from information from at least two sensors.

A method according to the invention improves the selectivity of the determination of an analyte using Gas Chromatography sensors.

A method according to the invention improves the selectivity of the determination of an analyte using CMOS sensors.

BRIEF DESCRIPTION OF THE DRAWINGS

The invention will be better understood and its various features and advantages will emerge from the following description of a number of exemplary embodiments and its appended figures in which.

DETAILED DESCRIPTION OF THE INVENTION

In this specification, the invention will be described by way of examples relative to GC and CMOS sensors. However the invention is not restricted to these sensors, and can be applied to any sensors for which a change of the value of a first physical parameter implies changes of a value of a second physical parameter representative of at least the concentration of an analyte.

Figure 1A:
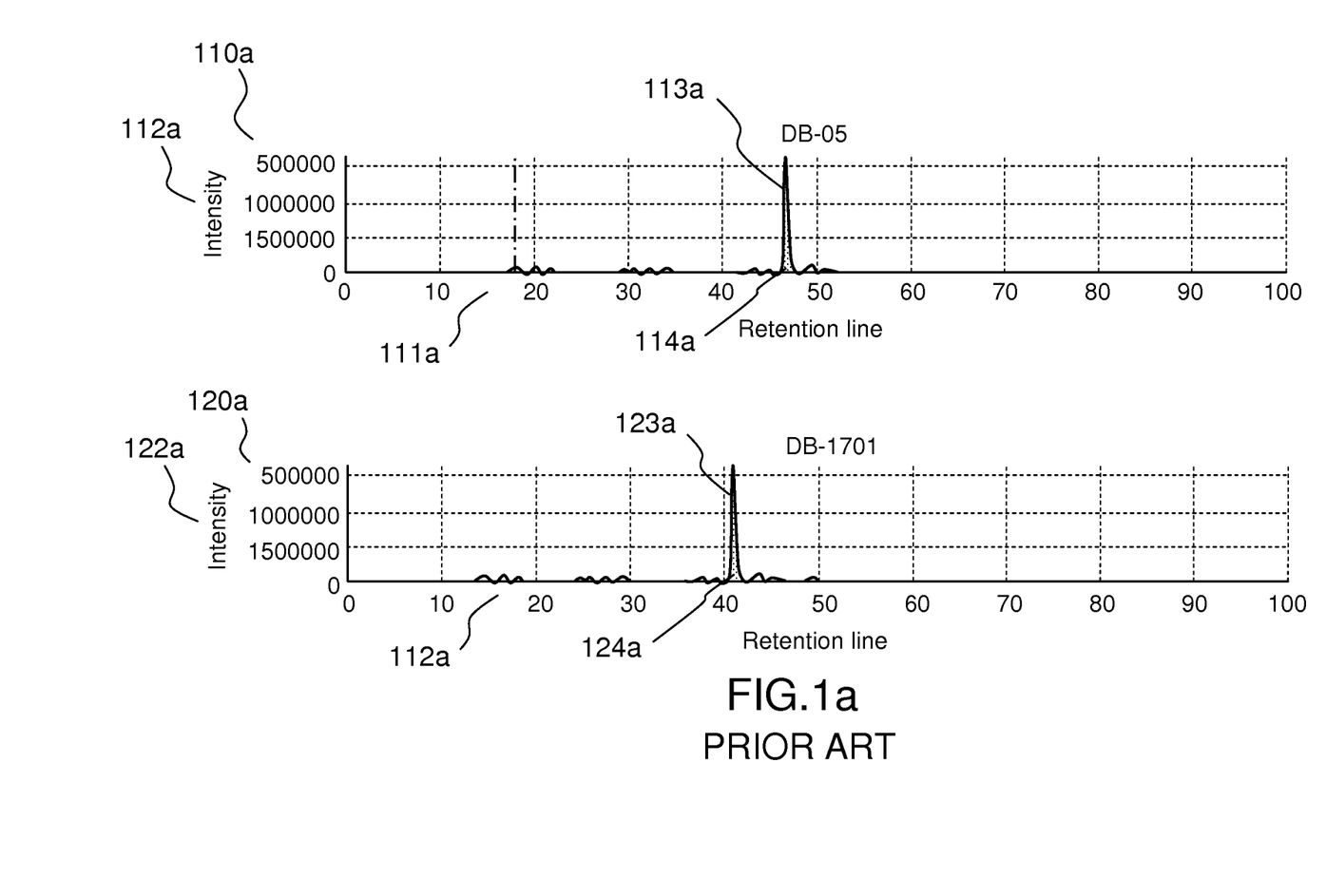
FIGS. 1a and 1b display respectively two examples of outputs of measurements in the prior art, respectively for gas chromatography and metal oxide sensors.
Figure 1B:
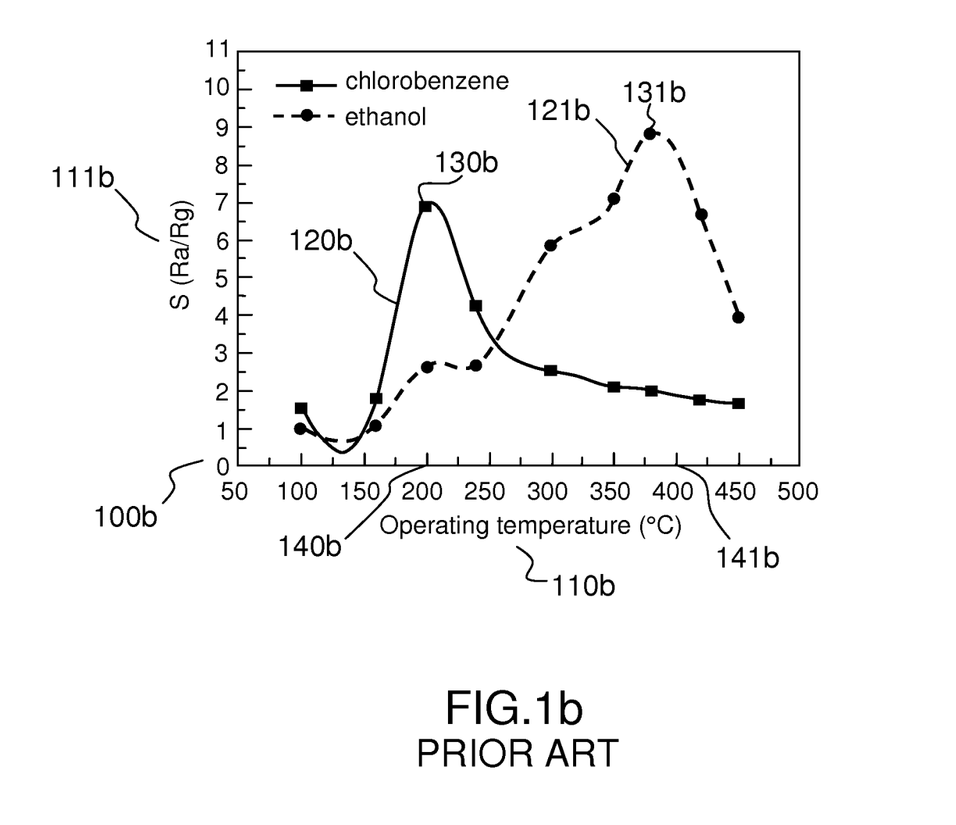

FIGS. 1a and 1b display respectively two examples of outputs of measurements in the prior art, respectively for gas chromatography and metal oxide sensors.

FIG. 1a displays an example of an output of measurement in the prior art, for two gas chromatography columns. The principle of a gas chromatography is notably disclosed by Pavia, Donald L., Gary M. Lampman, George S. Kritz, Randall G. Engel (2006). *Introduction to Organic Laboratory Techniques* (4th Ed.). Thomson Brooks/Cole. pp. 797-817. ISBN 978-0-495-28069-9. In Gas Chromatography a gaseous compound is sent along with a carrier gas in a column. The column has a microscopic layer of liquid or polymer that is called stationary phase. The stationary phase causes various analytes of the gas compound to cross the column during different durations and exit the column at different times. The duration for an analyte to travel through the column is called retention time. It depends on the type of analyte, the stationary phase, which defines the type of column, and other parameters such as the length of the column. In order to compare results of columns of the same type, retention times can be converted into a normalized measure called Kovats index. The Kovats index depends only on the analyte and the column type. Gas chromatography columns can be used for identifying analytes. To do so, a sensor is placed at the end of the column, which detects the quantity of particles which leave the column at any time.

Graphs 110a and 120a represent the output of sensing procedures using two Gas Chromatography sensors of two different types on the same gas compound, which contains a single analyte. They indicate, for each retention time represented on horizontal axis 111a, 112a, an intensity of measurement representative of the amount of particles that leaves the column at the retention time, said intensity being represented on vertical axis 112a, 122a. A peak of intensity 113a, 123a clearly appears at retention times 114a, 124a that characterize the analyte on the two columns. In this example, retention times 114a and 124a of the analyte in the two columns are different. The analysis of the retention time of a peak in a GC column, or the Kovats index of a peak in a GC column type, is an indication of the type of analyte, while the intensity of the peak is an indication of a relative amount of this analyte. Kovats index being a normalized measure, large database of reference Kovats index exist, for example the NIST database. Comparing a measured Kovats index to reference index in a database permits to identify a candidate analyte. However, a plurality of different analytes may have very similar retention times. It may therefore be difficult, observing a peak, to identify a peak among a plurality.

GC columns are manufactured by a plurality of companies, among which Agilent, Restek, Varian/Chrompack, Supelco. The type of column can be defined by a nomenclature of United States Pharmacopeial Convention (USP), the reference of the vendor, or the composition of the stationary phase. Examples of column types, defined by their USP nomenclature, the reference of the vendor Agilent, and the composition of the phase are given below:

| USP nomenclature | Ref. Agilent | Composition of the stationary phase |
|---|---|---|
| G46 | DB-1701 | 14% cyanopropyl phenyl, 86% dimethylpolysiloxane |
| G27, G36 | DB-5 | 5% diphenyl, 95% dimethyl polysiloxane |
| G1, G2, G38 | DB-1 | 100% dimethyl polysiloxane |
| G14, G15, G16, G20, G39 | DB-Wax | polyethylene glycol |

FIG. 1b displays an example of an output of measurement in the prior art, for a Complementary Metal Oxide Semiconductor (CMOS) gas sensor.

CMOS gas sensors are generally made of a heated plate of metal oxide sensor material. According to parameters that notably include the structure of the sensor, the material of the plate and the operating temperature, the sensor absorbs analytes that generate variations of the sensitivity of the plate. The measurement of the sensitivity of the plate allows the detection of analytes. Some CMOS gas sensors are very selective and react to precise analytes. Other types of CMOS sensors are able to detect a plurality of analytes, the variations of the sensitivity in contact to an analyte varying according to physical parameters such as the temperature of the plate, the wavelength of an UV pulse illuminating the plate, and the intensity of a current that polarizes the sensor.

Graph 100b represents the variation of the sensitivity of a CMOS gas sensor as a function of temperature, in contact with chlorobenzene and ethanol. Horizontal axis 110b indicate the operating temperature, and vertical axis indicates the sensitivity, expressed by the S(Ra/Rg) ratio. S(Ra/Rg) represents the ratio of the response of the sensor in contact to air (Ra) and to the fluid comprising the analyte (Rg). Curves 120b and 121b represents respectively the variation of sensitivity of the plate according to the operating temperature in presence of chlorobenzene and ethanol. These curves respectively have peaks 121b, 131b of intensity of sensitivity at operating temperatures 140b, 141b. Temperatures 140b, 141b of the peaks are representative of the type of analyte and the sensor, while the intensity of peaks 130b, 131b depends respectively on the relative amount of chlorobenzene and ethanol.

Figure 2:
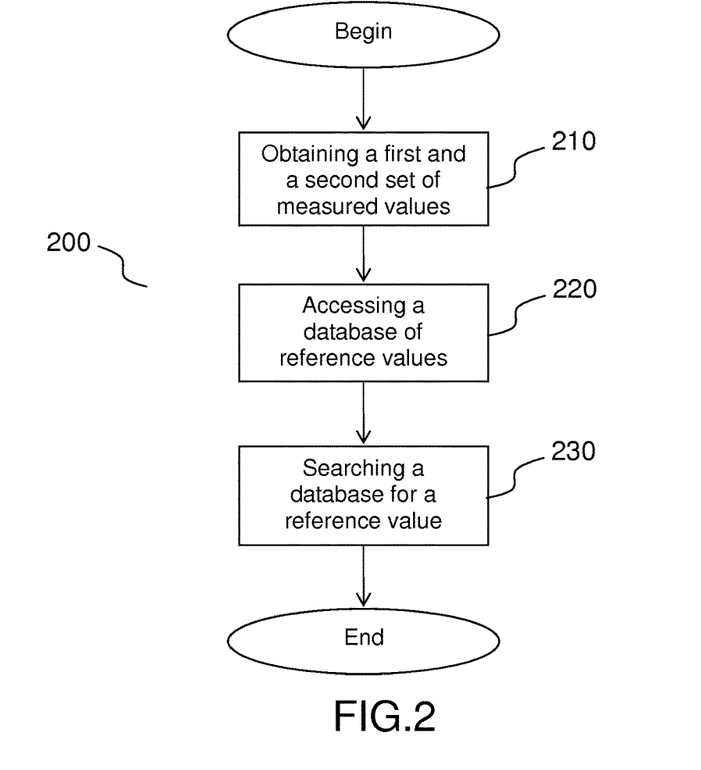
FIG. 2 displays an example of a method in an embodiment of the invention.

FIG. 2 displays an example of method in an embodiment of the invention.

A method according to the invention is a method for identifying an analyte in a fluid sensed by a group of sensors comprising a first sensor and a second sensor of different types. The type of sensor may refer to different sensing procedures. For example, the first and the second sensors of different types may be a GC sensor and a CMOS sensor. The type of sensor may also refer to sensors using the same sensing procedure, but with different structures. For example, the first and the second sensors of different types may be two GC sensors of two different type respectively, or two CMOS sensors with a plate made of two different materials.

A method according to the invention comprises a first step 210 for obtaining a first set of measured values from the first sensor of at least a first and a second physical parameters, said first parameter varying monotonically within a range of values, each value of the second parameter being associated with at least a value of the first parameter, said second parameter being representative of at least a concentration of the analyte and comprising at least a first local extremum for a first value of the first parameter. The step 210 also consists in obtaining a second set of values from the second sensor of at least a third and a fourth physical parameters, said third parameter varying monotically within a range of values, each value of the fourth parameter being associated with at least a value of the third parameter, said fourth parameter being representative of at least a concentration of the analyte and comprising at least a second local extremum for a second value of the third parameter.

In step 210 the first and the third physical parameter typically are operating parameters that vary monotonically within a range and for which measurements are taken. For example, for GC sensors displayed in FIG. 1a the first and third physical parameters would be retention times that vary between 0 and 100 s, while for CMOS sensors displayed in FIG. 1b it would be operating temperature that varies monotically between 100 and 450° C. Each measure of the first and third parameter is associated with a measure of the second and fourth parameter respectively, which is representative of at least a concentration of an analyte. For example in GC sensors displayed in FIG. 1a the second and fourth parameters would be the intensity of measurement on the vertical axis, while in CMOS sensors measurements displayed in FIG. 1b it would be the sensitivity of the sensor displayed on the vertical axis. The first local extremum for the first value and the second local extremum for the second value typically are the values of intensity of the peaks 113a, 123a, 130b, 131b, while the first and second values typically correspond to the values of retention time or temperature 114a, 124a, 140b, 141b at which the peaks occur.

A method according to the invention further comprises a second step 220 of accessing at least a database of reference values of the first parameter from a sensor of the same type as the first sensor, and reference values of the third parameter from a sensor of the same type as the second sensor. According to various embodiments of the invention, one or a plurality of databases of reference values can be accessed. Databases of reference values typically contain reference values of physical parameters at which a peak occurs for an analyte. Databases can for example contain reference retention times or Kovats indexes for different analytes for a GC column type. They may also contain operating temperatures at which a peak of intensity occurs when a type of CMOS sensor is in contact with an analyte.

Databases are typically constructed by capturing measurements with sensors on fluids of known analytes. They can be public databases like the NIST database for Gas Chromatography, or private databases built internally in a company. They may contain reference values related to a particular sensor, for example retention times for a GC column from a manufacturer, or normalized values that apply to a sensor type, for example reference Kovats indexes for analytes and a GC column type.

A method according to the invention further comprises a third step 230 for searching said at least a database for a reference value of the first parameter in relation to an extremum of the second parameter, and a reference value of the third parameter in relation to an extremum of the fourth parameter, close to the first value of the first parameter, respectively the second value of the third parameter.

This step typically consist, after having identified a value of the first and third parameters for which an extremum of the second and fourth parameters are found, searching reference values that are close in the database. Advantageously, this allows identifying, for at least two different types of sensors, the analytes whose reference values match the experimental values on two different types of sensors, and disambiguate the analytes to identify if two analytes have close reference values on a single sensor. For example, it may consist in identifying, in a database, reference Kovats indexes that are close to the Kovats index of a peak that is observed by a GC sensor.

In a number of embodiments of the invention, the method further comprises calculating a first ratio between the first local extremum and at least the second local extremum. This ratio is representative of the intensity of measurements between the two sensors. This embodiment is advantageous. Indeed, if two extrema for two sensors relate to the same analyte, at the same concentration, the ratio of values of the extrema should be representative of a ratio of sensitivity between the two sensors.

In a number of embodiments of the invention, this ratio of sensitivities depends only on the two sensors. It is therefore possible to obtain a second ratio of the sensitivities of the sensors by sensing a known analyte. For example, this ratio may be obtained by combining a first additional set of values from the first sensor and a second additional set of values from the second sensor of at least the first and the second physical parameters, respectively the third and the fourth physical parameters, for a second fluid comprising a known analyte. These sets can be obtained by measuring or retrieving pre-established sets, then accessing the at least a database, then searching the at least a database for an additional reference value of the first parameter in relation to an additional extremum of the second parameter in relation to the known analyte, and an additional reference value of the third parameter in relation to an additional extremum of the fourth parameter in relation to the known analyte, then calculating the second ratio between at least the additional extremum of the second parameter in the first additional set of values and at least the additional extremum of the fourth parameter in the second additional set of values.

This embodiment is advantageous, since it is possible to compare the values of the extrema of the second and fourth parameters even using a database that only contain values of the first and third parameters.

If a sensor is a GC column, this typically consists in performing series of measurements of intensity at different retention times for the known analytes, then searching a database of reference retention times or Kovats index for a reference retention time or Kovats index representative of a peak of intensity of the known analyte and the GC column type and identifying the associated value of intensity. Then it is possible to obtain a ratio representative of the intensities of measurements of two sensors for an identical concentration of a known analyte.

If a sensor is a CMOS sensor, series of measurements of sensitivity at different temperatures for the known analyte (or different values of a physical parameter that causes changes of sensitivity in contact with analytes) on two CMOS sensors. Then values of sensitivities occurring for values of known temperatures at which a peak of sensitivity occurs for the known analyte are stored, and a ratio representative of the differences of sensitivity of the two sensors for an identical concentration of analytes can be calculated.

It is also possible to calculate a ratio of the differences of sensitivity of two very different sensors, for example a CMOS and a GC sensors using a known analyte. As described above, it is possible to obtain, in a GC, a value of an area under the peak at a known reference Kovats index for the known analyte, and a value of sensitivity for a CMOS sensor at a known reference temperature of the known analyte. It is then possible to obtain a ratio representative of a difference of intensity between the two sensors. The same reasoning is possible for any pair of sensors of different types.

In other embodiments of the invention, the databases also contain reference values of the extremum of the second and fourth parameters for reference concentration of analytes. Therefore, it is possible to obtain directly a ratio between values of at least a local extremum of the reference values of the second parameter in relation with the reference value of the first parameter and at least a local extremum of the reference values of the fourth parameter in relation with the reference value of the third parameter. This embodiment is advantageous, since it is not necessary to perform additional measurements or calibrate the sensitivities of the sensors to have a reference value of the ratio of the second and fourth parameters.

In a number of embodiments of the invention, a score of relevance is attributed to an analyte, according to the closeness of the first value of the first parameter and the reference value of the first parameter for this analyte, the closeness of the second value of the third parameter and the reference value of the third parameter for this analyte, and a ratio between the first ratio between the first and the second extremum, and the second ratio representative of the differences of sensitivities of the two sensors.

In a number of embodiments of the invention, more than two sensors are available. In order to improve the relevancy of the score, a score can be computed for each pair of sensors, then a global score can be obtained, for example by averaging the scores for each pair of sensors.

EXAMPLE OF EMBODIMENT FOR TWO GAS CHROMATOGRAPHY COLUMNS

By means of non limitative example, an identification of an analyte can be performed with two Gas Chromatography columns using the invention. The two columns are respectively noted Ci and Cj. In Gas Chromatogrpahy, an analyte is generally characterized by a retention time or a Kovats Index, and the concentration of this analyte in a fluid by an area under a peak of intensity at this retention time or Kovats index.

In a first step, measurements are performed on the two Gas Chromatography Columns of different types Ci and Cj. At this stage a list of peaks, characterized by a Kovats index and a surface under the peak, can be identified. The identification of peaks in GC and the calculation of surfaces under the peaks are a common practice of men skilled in the art of gas sensing. They are for example disclosed by Robert L. Grob et all "*Modern Practice of gaz chromatography*". Wiley Interscience. fourth Edition (2004), or A. Wehrli and E. Kovats. '*Gas-chromatographische Charakterisierung organischer Verbindungen*. Teil 3: Berechnung der Retentionsindices aliphatischer, alicyclischer and aromatischer Verbindungen. Helv. Chim. Acta 42, 2709 (1959). In order to identify an analyte, theoretical Kovats indexes $K_{tCi}$ and $K_{tCj}$ of this analyte, on the two GC columns respectively, are retrieved from one of a plurality of databases. For example, theoretical Kovats indexes can be retrieved from the public NIST database, or from the AroChemBase developed by the applicant.

Then a corresponding peak can be identified for each column. For example, the peak whose Kovats index is the closest to the theoretical Kovats index of the tested analyte can be chosen. The experimental peaks have Kovats indexes $K_{rCi}$ and $K_{rCj}$ for the two columns respectively. They also have a surface under the peak Si and Sj respectively, for which it is possible to calculate a ratio $R_r(i,j)$ of the intensities of the two peaks. The ratio $R_r(i,j)$ equals for example $S_i/S_j$, or $S_j/S_i$.

Then a theoretical ratio $R_t(i,j)$ of areas under the peak for a identical concentration of an analyte is retrieve on these two columns is retrieved. This ratio can for example have been computed in a test phase of the two GC columns $C_i$ and $C_j$, during which a known concentration of a known analyte is tested, the ratio $R_t(i,j)$ being the ratio of the areas under the peak representative of the known analyte on the two columns.

A score of relevance CPnew(i,j) of the analyte can then be computed, for example by the formula:

$$CPnew(i, j) = 100 * \frac{\text{Min}(R_t(i, j), R_r(i, j))}{\text{Max}(R_t(i, j), R_r(i, j))} \times \frac{\text{Min}(K_{tCi}, K_{rCi})}{\text{Max}(K_{tCi}, K_{rCi})} \times \frac{\text{Min}(K_{tCj}, K_{rCj})}{\text{Max}(K_{iCj}, K_{rCj})}$$

In the formula above, the ratio $$\frac{\text{Min}(K_{tCi}, K_{rCi})}{\text{Max}(K_{tCi}, K_{rCi})}$$

is representative of the closeness of the theoretical and calculated Kovats indexes for this analyte on the first GC column. On the other hand, the ratio $$\frac{\text{Min}(K_{tCj}, K_{rCj})}{\text{Max}(K_{iCj}, K_{rCj})}$$

is representative of the closeness of the theoretical and calculated Kovats indexes for this analyte on the second GC column. Finally, the ratio $$\frac{\text{Min}(R_t(i, j), R_r(i, j))}{\text{Max}(R_t(i, j), R_r(i, j))}$$

is high if the ratio of the surfaces under the two calculated peaks matches the theoretical ratio of surface under the peak for a same concentration of a same analyte for the two columns. The latter ratio will on the contrary be low if the two identified peaks, even if being close to the theoretical peaks of the analyte, are representative of two different analytes.

This embodiment is therefore advantageous, since it correctly identifies an analyte not only if the observed peaks match the theoretical peaks on two different GC columns, but also if the ratio of the surfaces under the peak on the two columns shows that they have been generated by the same analyte.

In other embodiments of the invention, more than two GC columns are available. The method above can then be used for computing a score of relevance CPnew(i,j) for each pair of columns Ci and Cj, and compute a global relevancy score CPnew as the average of the score for each pair of columns. For example, if p different GC columns are used, p*(p−1)/2 different pair of columns can be defined. A global score of relevance can then be defined as:

$$CPnew = \frac{\sum_{i=1}^{p-1} \sum_{j=i+1}^{p} CPnew(i, j)}{p \times (p-1)/2}$$

Wherein CPnew(i,j) represents the score of relevance for the columns Ci and Cj, as defined above.

This embodiment is advantageous, since it allows to compute a global score on a larger number of columns, thereby making the score more precise, and the associated identification more robust.

EXAMPLE OF EMBODIMENT FOR TWO CMOS SENSORS

In an embodiment of the invention, two CMOS sensors of different types are used to identify an analyte within a fluid. The first CMOS sensor has a sensing layer made of $SnO_2$, while the second has a sensing layer made of CuO. The sensors provide a sensitivity response which varies according to the analytes present in the fluid and the temperature, as shown for example in FIG. 1b. This value is expressed by the ratio S(Ra/Rg). For effectuating series of measurements, the temperature of the sensing layer progressively increases between a minimum and a maximum temperature. A measure of sensitivity is performed at regular intervals, and a maximum of sensitivity due to the presence of an analyte can be observed at operating temperatures characterizing this analyte.

In an exemplary sensing procedure, the two CMOS sensors are operated between 300 and 500° C. The fluid contains a first analyte X and a method according to the invention will be used to attribute a score of relevance to the different analytes (for example acetylene, ethylene and CO). A maximum of sensitivity is observed on the first sensor at $T_1$=410° C., with $S_1$(Ra/Rg)=2.5 on the measurements from the first CMOS sensor $SnO_2$. A first maximum of sensitivity is observed on the second sensor at $T_2$=305° C., with $S_2$(Ra/Rg)=2.0.

Databases of values of temperatures characteristic of at least some analytes are then accessed for retrieving reference values of the operating temperature in which a maximum of sensitivity occur, for the two types of CMOS sensors. These databases may be public databases for these types of CMOS sensors. They may also be private databases, for example a vendor database of reference operating temperature for CMOS sensor whose access is furnished when delivering the CMOS sensor. The database notably comprise, for an analyte and a plurality of sensors: a reference temperature at which a peak of sensitivity occurs, and a reference value of the sensitivity. The sensitivities in the database have been obtained by sensing a fluid that contains an identical concentration of the analyte using the each sensor. Therefore, it is possible using this database to obtain a reference ratio of sensitivities for an analyte on two sensors.

In this example the following values are retrieved from a database or a plurality of databases of reference values of the temperature:

For analyte A Acetylene:
    Reference value of temperature on the first sensor:
        $T_{1A}$=400° C.; with $S_{1A}$(Ra/Rg)=2.92
    Reference value of temperature on the second sensor:
        $T_{2A}$=300° C.; with $S_{2A}$(Ra/Rg)=2.37

For analyte B Carbon monoxyde:
    Reference value of temperature on the first sensor:
        $T_{1B}$=350° C.; with $S_{1B}$(Ra/Rg)=0.27
    Reference value of temperature on the second sensor:
        $T_{2B}$=300° C.; with $S_{1B}$(Ra/Rg)=0.10

For analyte C Ethylene:
    Reference value of temperature on the first sensor:
        $T_{1C}$=500° C.; with $S_{1C}$(Ra/Rg)=0.41
    Reference value of temperature on the second sensor:
        $T_{2C}$=400° C.; with $S_{1C}$(Ra/Rg)=0.05

When attributing a score to the analyte X, the observed temperature $T_1$=410° C. is associated with $S_1$(Ra/Rg)=5, and the observed temperature $T_2$=305° C. is associated with $S_2$(Ra/Rg)=4.

Several embodiments are possible for attributing a score to an analyte using two sensors numbered i and j respectively.

In a number if embodiments of the invention a first ratio $R_r$ is calculated between at least the maximum of sensitivities on the first and the second sensors. This ratio may for example equal $R_{rX}=S_1(Ra/Rg)/S_2(Ra/Rg)=1.25$ for the unknown analyte X. This ratio is representative of the relative intensities of sensitivities of the two sensors when sensing the unknown analyte X.

In a number of embodiments of the invention a first second Rt is calculated between at least the maximum of sensitivities on the first and the second sensors using the reference values of the database. This ratio may for example equal $R_{tA}=S_{1A}(Ra/Rg)/S_{2A}(Ra/Rg)=1.23$ for analyte Acetylene, $R_{tB}g=S_{1B}(Ra/Rg)/S_{2B}(Ra/Rg)=2.65$ for analyte B carbon monoxyde and $R_{tC}=S_{1C}(Ra/Rg)/S_{2C}(Ra/Rg)=8.04$ for analyte C Ethylene. This ratio are respectively representative of the ratio of the sensitivities observed when the two sensors sense an identical concentration of the analytes A (Acetylene), B(Carbon monoxide) and C (Ethylene).

In this exemplary embodiment of the invention, a level of sensitivity for a reference concentration of the analyte is provided in the database with the reference temperature. The second ratio is therefore associated with the analyte that is being scored. In other embodiments of the invention, a unique ratio representative of the relative sensitivities of the two sensors is used. For example it may have been obtained by sensing a known analyte for which reference temperature of a maximum of sensitivity is known, and effectuating a ratio between the two sensitivities that have been obtained.

In a number of embodiments of the invention, a second additional ratio of at least the observed temperature for a maximum of sensitivity on the sensor i, noted and the corresponding theoretical temperature, noted $T_{tSi}$, is calculated. This ratio can be for example calculated by the following formula:

$$\frac{\text{Min}(T_{tSi}, T_{rSi})}{\text{Max}(T_{tSi}, T_{rSi})}.$$

This ratio is comprised between 0 and 1, is higher when the observed and reference temperatures are closer, and equals 1 if the observed and reference temperatures match exactly. Other formula are possible for the second additional ratio, for example:

$$1 - \frac{\text{Abs}(T_{tSi} - T_{rSi})}{\text{Max}(T_{tSi}, T_{rSi})}$$

More generally, in preferred embodiments formulas of a second additional ratio tend to generate higher values when the reference and observed temperatures for a peak of intensity on a first CMOS sensor are closer from each other.

Similarly, in a number of embodiments of the invention, a third additional ratio representative of the closeness of the observed temperature $T_{rSj}$ and the reference temperature $T_{tSi}$ of a maximum of sensitivity on the second sensor is calculated, for example by one of the formulas $$\frac{\text{Min}(T_{tSi}, T_{rSi})}{\text{Max}(T_{tSi}, T_{rSi})} \text{ and } 1 - \frac{\text{Abs}(T_{tSi} - T_{rSi})}{\text{Max}(T_{tSi}, T_{rSi})}.$$

In this example, the formula for calculating a score of relevance of an analyte on the two sensors is:

$$CP1(i, j) = 100 * \frac{\text{Min}(R_t(i, j), R_r(i, j))}{\text{Max}(R_t(i, j), R_r(i, j))} \times \frac{\text{Min}(T_{tSi}, T_{rSi})}{\text{Max}(T_{tSi}, T_{rSi})} \times \frac{\text{Min}(T_{tSj}, T_{rSj})}{\text{Max}(T_{tSj}, T_{rSj})}$$

Using the values of ratios and temperatures listed above, the score of relevance for the analyte A Acetylene is 94.58, the score of relevance for the analyte B carbon monoxide is 39.65 and the score of relevance for analyte C Ethylene is 9.72. This embodiment is therefore advantageous, since it provides a much higher score to the analyte A Acetylene, while both analyte A Acetylene and analyte B carbon monoxide have temperature that match a temperature of a peak of sensitivity on the second sensor. However the relative intensities of the peak were not representative of an identical concentration of analyte B on the two sensors, while it was for analyte A. Moreover, the attribution of a score to analytes remains valid even if the concentration that were used to build the database and the actual concentration that are sensed are different. Indeed the concentrations of Acetylene used for building the database were significantly lower than those used for identifying the unknown analyte: the sensitivities the first and the second sensor were 2.92 and 2.37 respectively in the database, and 5 and 4 in the actual measurement. Since the concentrations of acetylene were identical for the two sensors when building the database, and during the identification of the unknown analyte, the ratio of the sensitivities of the peaks are identical.

In yet other embodiments of the invention, reference temperatures and sensitivities may be obtained from a plurality of databases, or a single database built from a plurality of sources. This may for example be the case when a plurality of users enriches a collaborative database. In these cases the values of sensitivities can be associated with values of concentration of the analytes. For example a database may contain for an analyte Y, and two sensors S1 and S2:

A reference temperature, sensitivity and concentration $T_{1Y}$, $S_{1Y}$ and $C_{1Y}$ for the analyte Y on the sensor $S_1$;

A reference temperature, sensitivity and concentration $T_{2Y}$, $S_{2Y}$ and $C_{2Y}$ for the analyte Y on the sensor $S_2$.

In this case, the second ratio of intensity for the analyte Y for the two sensors S1 and S2 can be calculated using the sensitivities and relative concentrations of Y, for example using the formula:

$$RtY = \frac{S1Y * C2Y}{S2Y * C1Y}.$$

This formula permits to obtain a theoretical ratio of sensitivities that corrects the distortion generated by the different concentrations of Y used for building the database.

In other embodiments of the invention, physical parameters other than the temperature can be used for modifying the sensitivity of the CMOS sensor. For example the wavelength of an UV pulse that is used for increasing the sensitivity of the sensor can be used. It is well known that UV illumination with different wavelength provides different characteristics of sensitivity due to different photon energy. Moreover, specific wavelengths are linked to increased sensitivity in contact to specific gases. It is therefore possible to perform series of measurements of CMOS sensors with variations of a wavelength of an UV illuminating the plate of the CMOS sensor. Maxima of sensitivity can be observed on CMOS sensors at different wavelengths. When reference values of wavelengths that are associated to maxima of sensitivity are retrieved from a database, a method according to the invention can apply a score of relevance to an analyte according to the observed values of wavelength at which peaks of sensitivity appear, reference values of wavelength for an analyte and a sensor, and the values of the maxima of sensitivity.

In yet other embodiments of the invention, electric pulses of different intensities are used for modifying the sensitivity of a CMOS sensor to different gases. It is therefore possible to perform series of measurements of sensitivity for different values of intensity of an electric pulse. The sensitivity presents maxima at different intensities of electric pulse for different gases. It is then possible, by accessing reference values of the intensity of electric pulse that generate a maxima for a given analyte, to apply the method according to the invention to attribute a score of relevance to the analyte. More specifically, in an embodiment of the invention, maxima of sensitivities are identified for different values of the intensity of electric pulse. Using reference values of intensity of electric pulse to generate a maximum of intensity on a CMOS sensor for a given analyte, and the relative intensities of the maxima of sensitivities on two CMOS sensors, it is possible to use a method according to the invention to CMOS sensors using electric pulse as a first and third parameter.

The examples above are non-limitative. A large number of other embodiments are possible, while remaining within the scope of the invention. For example more than 2 CMOS sensors can be used and a global score be computed by averaging the scores generated by each pair. Similarly, a physical parameter other than temperature, wavelength of an UV pulse and intensity of an electric pulse can be modified for CMOS sensors to create extrema of sensitivity. In other embodiments of the invention, both CMOS and GC sensors may be used. The ratio representative of a similar concentration of an analyte may then for example be a ratio between an maximum sensitivity of a CMOS sensor and an area under a peak in GC. Other types of sensors can also be used. For example, the method may apply to electrophoresis.

Figure 3:
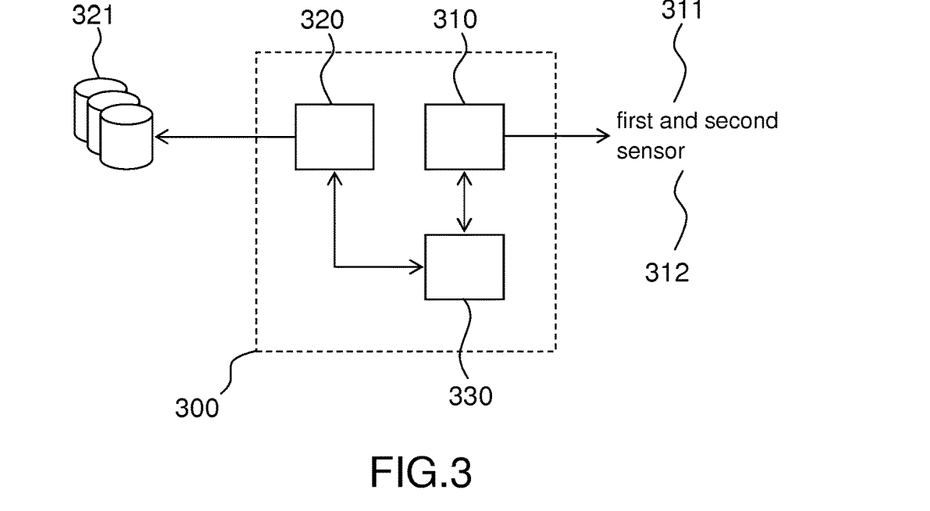
FIG. 3 displays an example of a device in an embodiment of the invention.

FIG. 3 displays an example of a device in an embodiment of the invention.

The device 300 is designed for identifying an analyte in a fluid sensed by a group of sensors comprising a first sensor 311 and a second sensor 312 of different types. The first sensor 311 and the second sensor 312 can for example be two GC columns of different types, two CMOS sensors of different types, or a GC column and a CMOS sensor. More generally, they can be sensors that associate to different values of a first physical parameter and a second value of a second physical parameter, representative of at least the concentration of the analyte.

The device 300 comprises a first module 310 configured for obtaining a first set of values from the first sensor 311 and a second set of values from the second sensor 311 of at least a first and a second physical parameters, respectively a third and a fourth physical parameters said first and third parameters varying monotonically within a range of values, each value of the second parameter and the fourth parameter being associated with at least a value of the first parameter, respectively at least a value of the third parameter, said second parameter and fourth parameter being representative of at least a concentration of the analyte and comprising at least a first local extremum for a first value of the first parameter, respectively a second local extremum for a second value of the third parameter.

The first module 310 may for example be in connection with the first sensor 311 and the second sensor 312, and launch the sensing procedure. It may also retrieve pre-established measurements performed by the first and the second sensors. The first and the second sensor may be embedded within the device. For example, the device 300 may be a portable device equipped with the first and the second sensor. It may also be a fixed device in connection with the first and the second sensor, or a device able to retrieve pre-established measurements from the first and the second sensor.

The device 300 further comprises a second module 320 for accessing at least a database 321 of reference values of the first parameter from a sensor of the same type as the first sensor, and reference values of the third parameter from a sensor of the same type as the second sensor. It may access a single database that contains both reference values of the first parameter and reference values of the third parameter or a first database for reference values of the first parameter and a second database for reference values of the second parameter. It may also access a plurality of databases of reference values of the first parameter and/or a plurality of databases of reference values of the third parameter. It may access public databases, for example the NIST database of Kovats indexes, or privately built databases such as the AroChem-Base database.

In an embodiment of the invention, a copy of the at least a database 321 is present on the device. In other embodiments of the invention, the database or plurality of databases 321 is accessed remotely, for example using an internet or private network.

The device 300 further comprises a third module 330 for searching said at least a database for a reference value of the first parameter in relation to an extremum of the second parameter, and a reference value of the third parameter in relation to an extremum of the fourth parameter, close to the first value of the first parameter, respectively the second value of the third parameter.

In a number of embodiments of the invention, the third module 300 may be further configured for computing a ratio between a first and a local extremum, and a reference ratio for the two sensors, and more generally the third module can be configured for implementing the steps of any embodiment of the method 300.

The third module 300 is described as a logical module. It may for example be implemented using a microcontroller, a Central Processing Unit (CPU) or any other computational means.

Figure 4A:
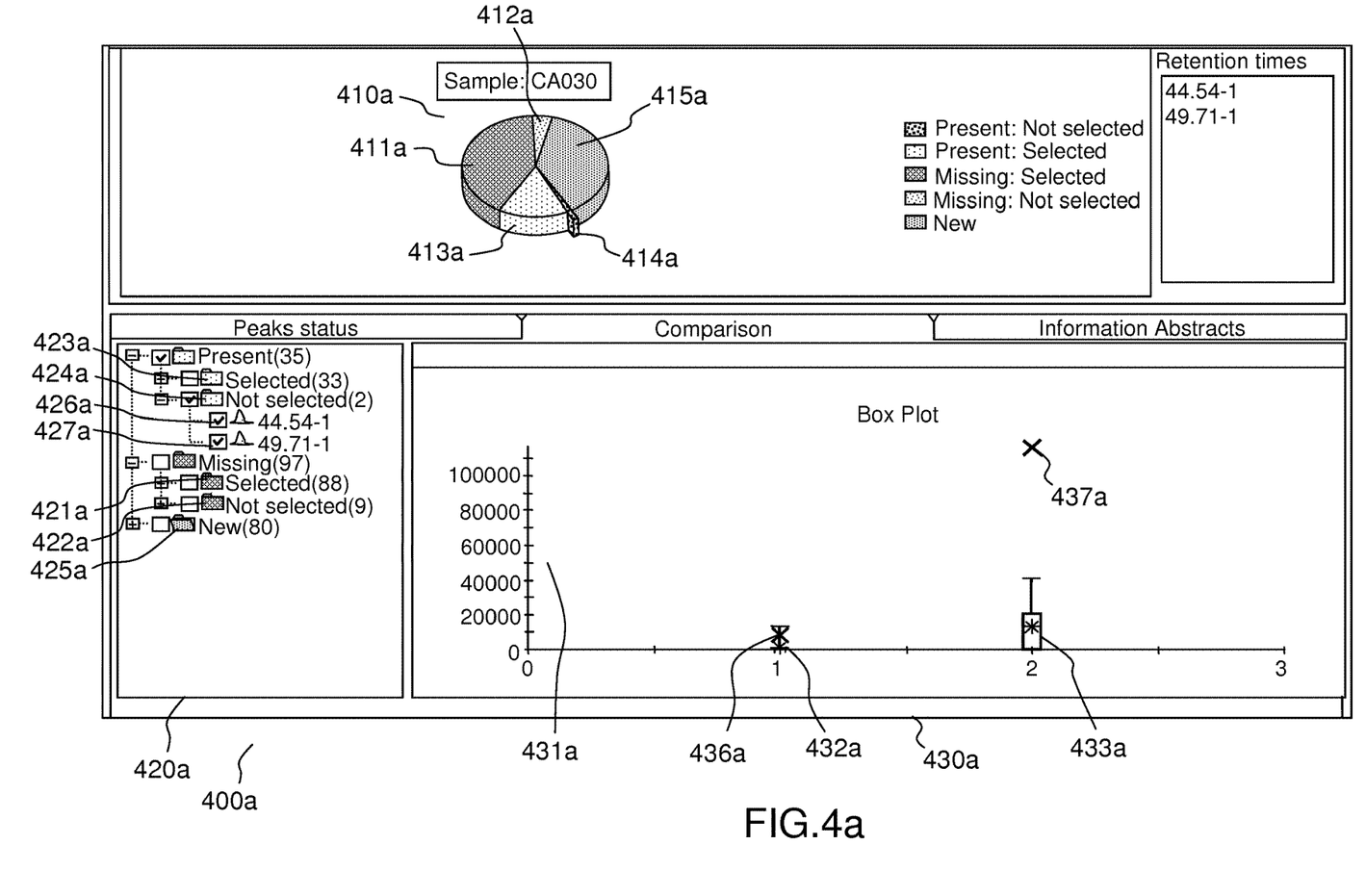
FIGS. 4a, 4b and 4c display three examples of interface for identifying an analyte and enriching a collection of observations using a method in an embodiment of the invention.
Figure 4B:
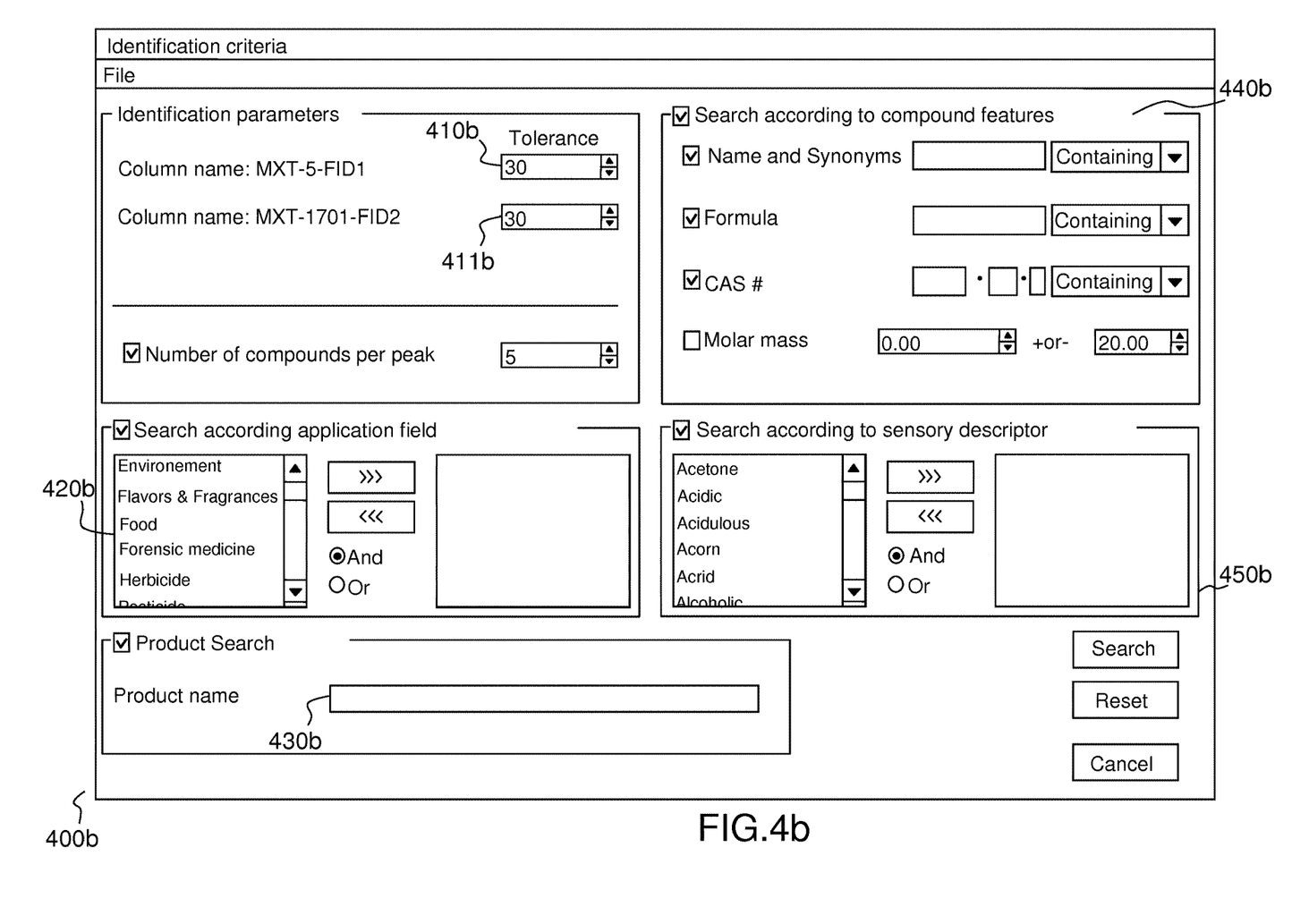
Figure 4C:
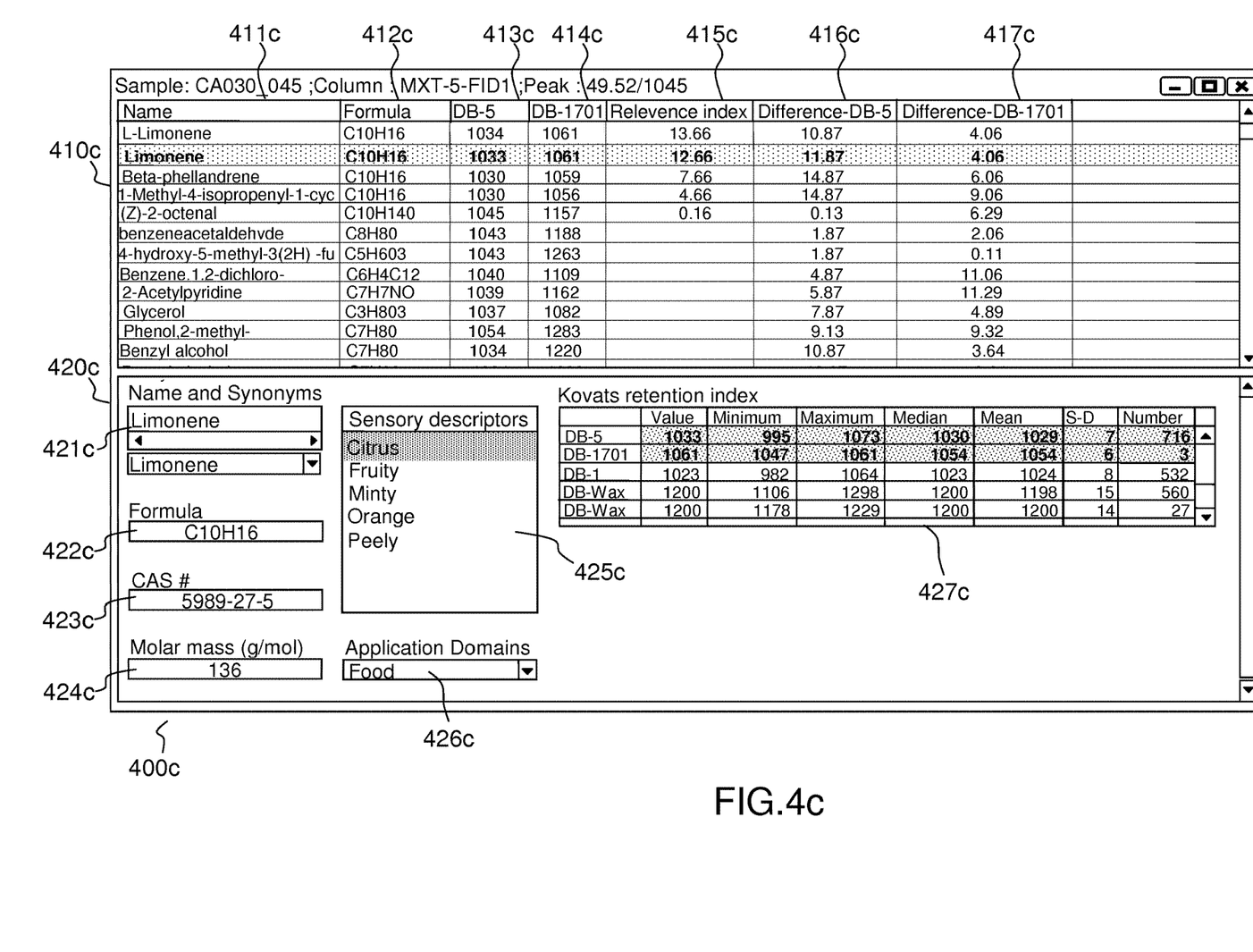

FIGS. 4a, 4b and 4c display three examples of interface for identifying an analyte and enriching a collection of observations using a method in an embodiment of the invention.

The FIG. 4a displays an example of interface 400a for identifying an analyte in an embodiment of the invention. This interface can for example be part of software for identifying analytes.

The interface comprises a discus 410a. This discus represents peaks that have been identified or not during a GC sensing procedure. After applying a GC sensing procedure to a fluid, a plurality of peaks appear in the GC, in relation to the analytes present in the fluid. Afterwards, peaks are compared to peaks in relation to known analytes in a collection of observed peaks. This type of comparison is notably disclosed by the U.S. Pat. No. 7,734,436 of the same applicant. U.S. Pat. No. 7,734,436 separates the peaks of a GC in three different classes:

The class "Present" for the peaks that are present in the fluid and the collection of observed peaks;
The class "Missing" for the peaks that are present in the collection of observed peaks but not in the fluid;
The class "New" for the peaks which are present in the fluid but unknown in the collection of observed peaks.

In addition of the disclosure of U.S. Pat. No. 7,734,436, the interface 400a splits the class "Present" in two classes "Present—selected" and "Present—not selected" and the class "Missing" in two classes "Missing—selected" and "Missing—not selected". The discus displays the relative proportion of the peaks that belong to the classes "Missing—selected" 411a, "Missing—not selected" 412a, "Present—selected" 413a, "Present—not selected" 414a and "New" 415a.

The sub-window 420a permits a precise selection of the peaks. The peaks of the classes "Missing—selected", "Missing—not selected", "Present—selected", "Present—not selected" and "New" can be selected by respectively expanding the boxes 421a, 422a, 423a, 424a and 425a. In the example displayed, the box 424a have been expanded and the peaks under the boxes 426a and 427a have been selected, which belong to the class "Present—not selected".

The sub-window 430a displays the comparison of the peaks selected and the possible equivalents in the collection of observed peaks. A scale of intensity is defined on vertical axis 431a. The intensities of the two peaks are respectively displayed by stars 436a and 437a. The known intensities in the collection of observed peaks for the Kovats indexes of the two peaks are respectively displayed by bars 432a and 433a.

The FIG. 4b displays a window 400b for selecting a subset of analytes to identify. Due to the large number of possible analytes to sense, it may be interesting to attribute a score to only a subset of analytes of a database. The window 400b can be used for selecting a subset of possible analytes in the database "AroChem Base" developed by the applicant. In this example the fluid is sensed by two chromatography columns, of two different types, the GC columns DB-5 and DB-1701 from Agilent, whose stationary phase are respectively "05% Phenyl 95% Dimethyl Polysiloxane" and "14% Cyanopropyl-phenyl 86% dimethyl polysiloxane".

The two fields 410b and 411b under "Tolerance" are used for restricting the analytes to those which present a peak of intensity around the peaks selected within the tolerance. The sub-window 420b is used for restricting the search to analytes that belong to application fields, such as "Environment", "Flavor & Fragrances", "Food", etc. . . . . The field 430b can be used for searching directly a product name, while the sub-window 440b is used for filtering analytes that correspond to certain features, and the sub-window 450b for searching analytes that correspond to sensory descriptors.

The FIG. 4c displays a window 400c that presents the possible analytes, along with a score of relevance calculated by a method according to the invention, for example the method 200.

The sub-window displays the possible analytes for identification. Each line represents an analyte. The column 411c represents the name of the analyte. The column 412c displays its chemical formula. The column 413c displays its Kovats index for the GC column DB-05. The column 414c displays its Kovats index for the GC column DB-1701. The column 415c displays the relevance index, calculated by a method according to the invention. The column 416c displays the difference of the observed and theoretical Kovats indexes for this analyte on the GC column DB-05. The column 417c displays the difference of the observed and theoretical Kovats indexes for this analyte on the GC column DB-17.

The sub-window 420c displays information about an analyte whose line have been selected in sub-window 410c, in this example the analyte "Limonene" of the second line of the sub-window 410c. It notably displays its name 421c, its formula 422c, a number of identification 423c, its molar mass 424c, a list 425c of sensory descriptors that apply to this analyte, a list 426c of application domains, and a table 427c of comparative Kovats indexes on a plurality of columns types. The number iof identification 423c can be a Chemical Abstracts Service (CAS) Registry Number, which is an unique number representative of a chemical substance. The CAS Registry Number is widely accepted in scientific literature and is for example described in the webpage http://en.wikipedia.org/wiki/CAS_Registry_Number.

The examples of graphical interfaces for identification relate to GC column sensing. However, the invention and identification can be applied to any sensor for which a physical parameter representative of at least the concentration of analyte varies according to a physical parameter. For example the Kovats indexes may be replaced by temperature for CMOS sensors whose sensibility to analytes vary with the temperature, while the relevance indexes in column 415c are adapted to the sensors available.

The examples described above are given as illustrations of embodiments of the invention. They do not in any way limit the scope of the invention which is defined by the following claims.

The invention claimed is:

1. A method for identifying an analyte in a fluid sensed by a group of sensors comprising a first sensor and a second sensor of different types, said method comprising:—obtaining a first set of values from the first sensor of at least a first and a second physical parameters, said first parameter varying monotonically within a range of values, each value of the second parameter being associated with at least a value of the first parameter, said second parameter being representative of at least a concentration of the analyte and having a first extremum value associated with a first value of the first parameter;

obtaining a second set of values from the second sensor of a third and a fourth parameter, said third parameter varying monotonically within a range of values, each value of the fourth parameter being associated with at least a value of the third parameter, said fourth parameter being representative of at least a concentration of the analyte and having a second extremum value associated with a first value of the third parameter;

accessing at least a database of reference values of the first parameter from a sensor of the same type as the first sensor, and reference values of the third parameter from a sensor of the same type as the second sensor;

searching said at least a database for a reference value of the first parameter in relation to an extremum of the second parameter, and a reference value of the third parameter in relation to an extremum of the fourth parameter;

identifying the analyte based at least on a first ratio between at least the first extremum value and at least the second extremum value.

2. The method of claim 1, wherein the reference value of the first parameter is the value of the first parameter present in the database which is the closest to the first value of the first parameter, and the reference value of the third parameter is the reference value of the third parameter present in the at least a database which is the closest to the first of the third parameter.

3. The method of claim 1, wherein the reference value of the first parameter is any value of the first parameter present in the database, and the reference value of the third parameter is any value of the third parameter present in the database.

4. The method of claim 1, further comprising:
obtaining a second ratio, said second ratio being calculated by a method comprising:
obtaining a first additional set of values from the first sensor and a second additional set of values from the second sensor of at least the first and the second physical parameters, respectively the third and the fourth physical parameters, for a second fluid comprising a known analyte;
searching the at least a database for an additional reference value of the first parameter in relation to an additional extremum of the second parameter in relation to the known analyte, and an additional reference value of the third parameter in relation to an additional extremum of the fourth parameter in relation to the known analyte;
calculating the second ratio between at least the additional extremum of the second parameter in the first additional set of values and at least the additional extremum of the fourth parameter in the second additional set of values.

5. The method of claim 1, wherein the at least a database further comprises reference values of the second parameter from a sensor of the same type than the first sensor, and reference values of the fourth parameter from a sensor of the same type than the second sensor, comprising:
obtaining a second ratio, between at least an extremum of the reference values of the second parameter in relation with the reference value of the first parameter and at least and extremum of the reference values of the fourth parameter in relation with the reference value of the third parameter.

6. The method of claim 4, further comprising computing a score for the analyte, said score being obtained by performing at least the product of;
a first additional ratio of the minimum of the second ratio and the first ratio to the maximum of the second ratio and the first ratio;
a second additional ratio of the minimum of the first value of the first parameter and the reference value of the first parameter to the maximum of the first value of the first parameter and the reference value of the first parameter;
a third additional ratio of the minimum of the first value of the third parameter and the reference value of the third parameter to the maximum of the first value of the third parameter and the reference value of the third parameter.

7. The method of claim 6, comprising calculating a plurality of scores for a plurality of analytes respectively, displaying to an operator said plurality of scores for said plurality of analytes.

8. The method of claim 1, wherein at least one of the first and the second sensor is a Gas Chromatography Column and at least one of the first and the third physical parameter is one of a retention time and a Kovats index.

9. The method of claim 8, wherein the database is the NIST database.

10. The method of claim 1, wherein at least one of the first and the second sensor is a metal oxide sensor, at least one of the first and the third physical parameter is one of a temperature, a wavelength of an UV illumination, or an intensity of an electric pulse, and at least one of the second and the first physical parameter is a value of sensitivity.

11. A method for identifying an analyte in a fluid sensed by a group of sensors comprising at least three sensors of different types, said method comprising:
calculating, for each possible pair of sensor comprising a first and a second sensor chosen in the at least three sensors, a pair score of the analyte based on a first ratio calculated using a method according to claim 1;
calculating a global score of the analyte by averaging the sensor pair scores.

12. A device for identifying an analyte in a fluid sensed by a group of sensors comprising a first sensor and a second sensor of different types, said device comprising:
a first module configured for:
obtaining a first set of values from the first sensor of at least a first and a second physical parameters, said first parameter varying monotonically within a range of values, each value of the second parameter being associated with at least a value of the first parameter, said second parameter being representative of at least a concentration of the analyte and having a first extremum value associated with a first value of the first parameter;
obtaining a second set of values from the second sensor of at least a third and a fourth physical parameters, said third parameter varying monotonically within a range of values, each value of the fourth parameter being associated with at least a value of the third parameter, said fourth parameter being representative of at least a concentration of the analyte and having second extremum value for a first value of the third parameter;
a second module configured for accessing at least a database of reference values of the first parameter from a sensor of the same type than the first sensor, and reference values of the third parameter from a sensor of the same type as the second sensor;
a third module configured for searching said database for a reference value of the first parameter in relation to an extremum of the second parameter, and a reference value of the third parameter in relation to an extremum of the fourth parameter;
a fourth module configured for identifying the analyte based at least on a first ratio between at least the first extremum value and at least the second extremum value.

13. A computer program product, stored on a non-transitory computer readable medium, configured for identifying an analyte in a fluid sensed by a group of sensors comprising a first sensor and a second sensor of different types, said computer program product comprising:
code means for obtaining a first set of measured values from the first sensor of at least a first and a second physical parameters, said first parameter varying monotonically within a range of values, each value of the second parameter being associated with at least a value of the first parameter, said second parameter being representative of at least a concentration of the analyte and having a first extremum value for a first measured value of the first parameter;
code means for obtaining a second set of measured values from the second sensor of a third and a fourth physical parameters, said third parameter varying monotonically within a range of values, each value of the fourth parameter being associated with at least value of the third parameter, said fourth parameter being representative of at least a concentration of the analyte and having a second extremum value associated with a first measured value of the third parameter;

code means for accessing at least a database of reference values of the first parameter from a sensor of the same type than the first sensor, and reference values of the third parameter from a sensor of the same type as the second sensor;

code means for searching said database for a reference value of the first parameter in relation to an extremum of the second parameter, and a reference value of the third parameter in relation to an extremum of the fourth parameter;

code means for identifying the analyte based at least on a first ratio between at least the first extremum value and at least the second extremum value.

* * * * *